United States Patent
Kelch et al.

(10) Patent No.: US 8,297,753 B2
(45) Date of Patent: Oct. 30, 2012

(54) METHOD FOR DETERMINING CORRECTION CHARACTERISTICS FOR A VISION AID

(75) Inventors: Gerhard Kelch, Aalen (DE); Timo Kratzer, Aalen (DE)

(73) Assignee: Carl Zeiss Vision GmbH, Aalen (DE)

( * ) Notice: Subject to any disclaimer, the term of this patent is extended or adjusted under 35 U.S.C. 154(b) by 0 days.

(21) Appl. No.: 12/376,868

(22) PCT Filed: Aug. 1, 2007

(86) PCT No.: PCT/EP2007/006789
§ 371 (c)(1),
(2), (4) Date: May 26, 2009

(87) PCT Pub. No.: WO2008/017404
PCT Pub. Date: Feb. 14, 2008

(65) Prior Publication Data
US 2010/0118265 A1    May 13, 2010

(30) Foreign Application Priority Data
Aug. 8, 2006 (DE) .................. 10 2006 036 958

(51) Int. Cl.
*A61B 3/00* (2006.01)

(52) U.S. Cl. ........................ 351/246; 351/205

(58) Field of Classification Search .......... 351/246, 351/205
See application file for complete search history.

(56) References Cited

U.S. PATENT DOCUMENTS

| | | | |
|---|---|---|---|
| 6,511,180 B2 | 1/2003 | Guirao et al. | |
| 2002/0140902 A1 | 10/2002 | Guirao et al. | |
| 2004/0169820 A1 | 9/2004 | Dai et al. | |
| 2005/0057723 A1* | 3/2005 | Wakil et al. | 351/246 |
| 2005/0134799 A1* | 6/2005 | Thompson et al. | 351/222 |
| 2006/0023162 A1* | 2/2006 | Azar et al. | 351/246 |

FOREIGN PATENT DOCUMENTS

| | | |
|---|---|---|
| WO | 02/083078 A2 | 10/2002 |
| WO | 03/032825 A1 | 4/2003 |
| WO | 2005/070285 A1 | 8/2005 |

* cited by examiner

*Primary Examiner* — James Greece
(74) *Attorney, Agent, or Firm* — GrayRobinson, PA

(57) ABSTRACT

A method for determining correction characteristics for a vision aid for at least one eye of a person wherein: a vision impression of the person is determined in a first usage condition after which a vision impression of the person is determined in a second usage condition after which the wavefront of the person is optimized by determining the correction characteristics for the vision aid until the vision impression of the person in the second usage condition at least approximately matches the vision impression of the person in the first usage condition.

14 Claims, 1 Drawing Sheet

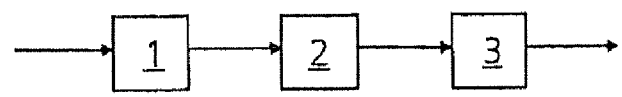
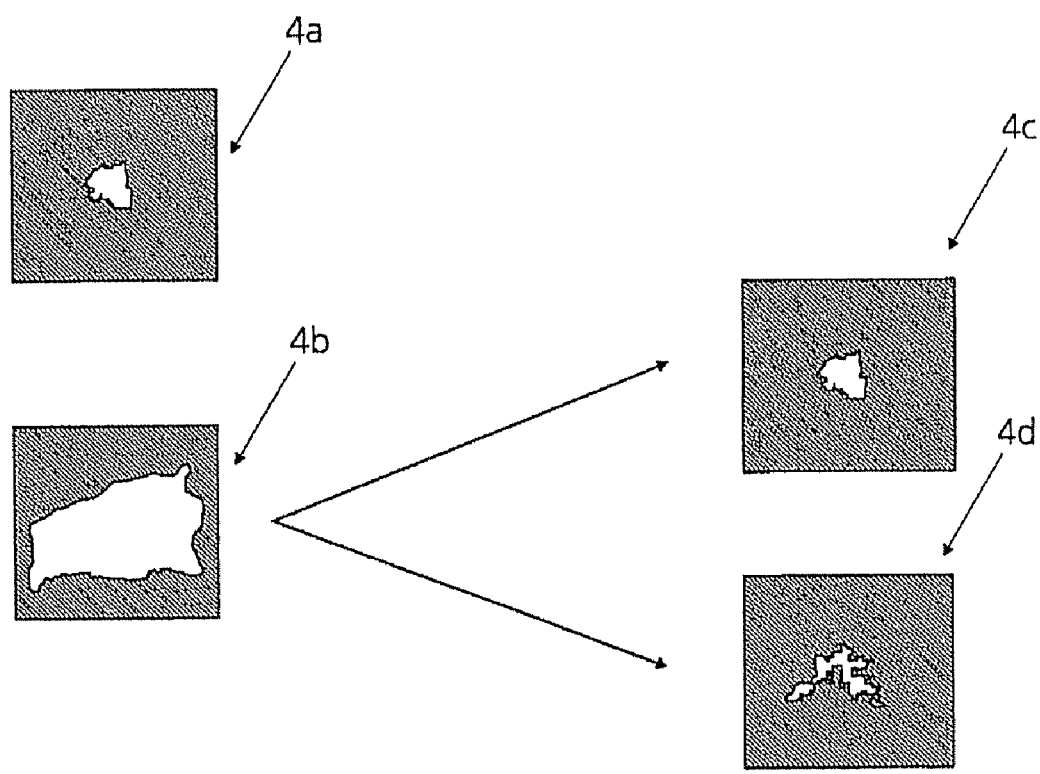
Fig. 1
Fig. 2

METHOD FOR DETERMINING CORRECTION CHARACTERISTICS FOR A VISION AID

CROSS-REFERENCE TO RELATED APPLICATIONS

This application claims priority under 35 U.S.C. Sections 119(a)-(d), 120, 363 and 365 to PCT/EP2007/006789, filed Aug. 1, 2007 which designated the United States and at least one other country in addition to the United States and claimed priority to German Application No. 10 2006 036 958.0 filed Aug. 8, 2006. The specifications of these applications are expressly incorporated by reference into this application in their entirety.

FIELD OF THE INVENTION

The invention relates to a method for determining correction characteristics of a visual aid for at least one eye of a person.

Known methods for calculating the characteristics of visual aids and/or spectacle lenses proceed in a purely mathematical/optical fashion. In this process, the errors are minimized to an absolute value of zero, the individual physiology of the spectacle wearer not being taken into account in the processing of the retinal image. Consequently, the characteristics of the spectacle lenses that are determined do not necessarily correspond to the characteristics desired by the spectacle wearer with regard to visual quality.

BACKGROUND OF THE INVENTION

U.S. Pat. No. 6,511,180 B2 relates to a method and a system for determining a refractive correction for a human eye and includes objective measurement of higher order wavefront errors and accurate estimation of the subjective refraction.

WO 02/083078 A2 relates to a method for determining an ocular refraction, the aim being to attain a desired quality with regard to a selected visual characteristic. To this end, wavefront errors are measured in order to objectively determine the status of the ocular refraction. It is stated that the visual quality of an accumulative result of the ocular refraction is among many different conditions of use. The desired visual quality can differ for various primary requirements of the individual patients. These various requirements can relate, for example, to night vision. Objective and subjective refraction measurements are carried out on test subjects in order to determine correlations that are later applied to new patients. There is no individual measurement. In order to achieve a desired visual quality, a refraction is measured, and the latter is described by a mathematical function. Thereafter, this mathematical function is optimized in order to improve the prescribed visual characteristic in the scope of the visual quality.

SUMMARY OF THE INVENTION

The object of the present invention is to provide a method of the type mentioned at the beginning that improves the individual visual comfort for the wearer of the visual aid.

This object is achieved according to the invention by claim 1.

The inventive method takes into account the subjective sensitivity of the wearer of the visual aid or of the spectacle wearer, there being carried out optimization to a specific absolute error magnitude at which an individual optimum of visual comfort is attained for the respective wearer under physiological aspects. The visual comfort is thereby substantially improved for the person.

This is carried out for each individual person, in particular for each eye of the person by optimization with regard to the matching of the visual impression of the person under two usage conditions, preferably in the light and in the dark. Firstly, in particular, the wavefront error and the subjective refraction are measured, or a spectacle measurement is carried out, under the first usage condition (for example in the light) in order to determine the visual impression of the person. Thereafter, under the second usage condition (for example in the dark) the visual impression of a person is determined in turn, in particular by measuring the wavefront error, which usually differs from the wavefront error under the first usage condition (for example different pupillary aperture in the light/dark). The lower order wavefront errors are then corrected under the second usage condition so as to produce a visual impression as under the first usage condition. The person's wavefront is, as it were, optimized until the visual impressions under the two usage conditions at least approximately match. The person thus obtains an optimum visual impression in the light, there being no need to adapt to the dark. Glare in bright sunshine could also come into consideration as a further usage condition.

In addition, various further metrics can be taken into account in parallel as so-called metametrics, preferably a point spread function, a contrast vision and/or a dynamic vision.

Both spectacle lenses and contact lenses or the like come into consideration as a visual aid.

The result is thus advantageously a complete visual impression that has as many as possible, or all of the instances of defective vision in the eyes of the person. This total visual impression can then be optimized.

BRIEF DESCRIPTION OF THE DRAWINGS

An exemplary embodiment of the invention is described below in principle with the aid of the drawing.

In the drawing:

FIG. 1 shows a greatly simplified flowchart of an inventive method; and

FIG. 2 shows an illustration of the operation of the inventive method.

DETAILED DESCRIPTION OF THE INVENTION

FIG. 1 illustrates a flowchart of an inventive method for determining correction characteristics of a visual aid for at least one eye of a person, an individual physiology of the person being taken into account in the processing of the retinal image in order to attain an individual optimum of visual comfort for the person.

In this case, in a first step 1, a visual impression of the person in the light is determined as first usage condition by means of a wavefront error measurement and/or a measurement of a subjective refraction. The wavefront error measurement is performed in a known way by a device that, as it were, determines the geometry of the eye. The determination of the subjective refraction is performed by placing different test lenses in front of the person's eyes, an optimum test lens being determined. The sphere-cylinder axis (SCA) is determined from the wavefront error terms or lower order zernike coefficients in order to correct the visual acuity (power of vision) for the lenses of the visual aid.

Thereafter, in a second step 2, a visual impression of the person is determined in the dark as a second usage condition by a wavefront error measurement.

In a third step 3, the wavefront of the person, that is to say the lower order wavefront error terms or the correction characteristics of the visual aid, are optimized until the visual impression of the person in the dark at least approximately matches the visual impression of the person in the light.

Visual impressions 4a to 4d, which are described by a point spread function as metametric, are illustrated in FIG. 2 by way of example and in a greatly simplified fashion. The visual impression 4a results with the visual aid in the light. The visual impression 4b is produced in the dark without the visual aid. The result of applying the inventive method is advantageously a visual impression 4c with the visual aid in the dark that at least approximately matches the visual impression 4a. The person therefore need not adapt to the dark. By way of example, in known methods the result is the visual impression 4d that does not match the visual impression 4a, the person disadvantageously having to adapt. The visual comfort therefore drops substantially.

In other exemplary embodiments, various further metrics could be taken into account in parallel as so-called metametrics, preferably contrast vision or dynamic vision.

We claim:

1. A method for determining correction characteristics of a visual aid for at least one eye of a person, said method comprising the steps of:
    determining a visual impression of the person viewing with the eye under a first usage condition, said visual impression of said person under said first usage condition being determined based on at least one of, a wavefront error measurement and a measurement of a subjective refraction;
    determining a visual impression of the person viewing with the eye under a second usage condition, said visual impression of said person under said second usage condition being determined based on a wavefront error measurement, said first usage condition differing from said second usage condition as to an amount of light under which said viewing with the eye is carried out; and,
    determining the correction characteristics of the visual aid such that a point spread function describing a visual impression of the person viewing with the eye visually aided by a visual aid having said correction characteristics under said second usage condition at least approximately matches a point spread function describing a visual impression of the person viewing with the eye visually aided by a visual aid having said correction characteristics under said first usage condition.

2. A method as claimed in claim 1, wherein said first usage condition comprises a condition under which the eye carries out viewing in light.

3. A method as claimed in claim 1 or 2, wherein said second usage condition comprises a condition under which the eye carries out viewing in the dark.

4. A method as claimed in claim 1, 2 or 3, wherein further metrics are used in parallel to determine each said visual impression.

5. A method as claimed in claim 4, wherein said further metrics comprise at least one of: a point spread function, a contrast vision and a dynamic vision.

6. A method as claimed in claim 1, 2, 3, 4, or 5, wherein said visual aid comprises a spectacle lens.

7. A method for determining correction characteristics of a visual aid for at least one eye of a person, said method comprising the steps of:
    determining a visual impression of the person viewing with the eye under a first usage condition;
    determining a visual impression of the person viewing with the eye under a second usage condition, said second usage condition being different from said first usage condition;
    determining the correction characteristics of the visual aid such that a point spread function describing a visual impression of the person viewing with the eye visually aided according to said correction characteristics under said second usage condition at least approximately matches a point spread function describing a visual impression of the person viewing with the eye visually aided according to said correction characteristics under said first usage condition.

8. A method according to claim 7 wherein said first usage condition comprises a condition under which the eye carries out viewing in light and said second usage condition comprises a condition under which the eye carries out viewing in dark.

9. A method as claimed in claim 7, wherein said first usage condition comprises a condition under which the eye carries out viewing in light.

10. A method as claimed in claim 7, wherein said second usage condition comprises a condition under which the eye carries out viewing in dark.

11. A method as claimed in claim 7 wherein said first usage condition comprises a condition in which the eye carries out viewing under more light than is present under said second usage condition.

12. A method as claimed in claim 7, wherein said second usage condition comprises a condition in which the eye carries out viewing under less light than is present under said first usage condition.

13. A method as claimed in claim 1 or 7, wherein said step of determining a visual impression of the person viewing with the eye under said first usage condition comprises viewing with the eye being visually aided.

14. A method as claimed in claim 1 or 7, wherein said step of determining a visual impression of the person viewing with the eye under said second usage condition comprises viewing with the eye being visually unaided.

* * * * *